(12) United States Patent
Scolari

(10) Patent No.: US 8,870,165 B2
(45) Date of Patent: Oct. 28, 2014

(54) APPARATUS FOR DISTRIBUTING A FRAGRANCE USING A FAN

(76) Inventor: Nathan A. Scolari, Greenville, SC (US)

( * ) Notice: Subject to any disclaimer, the term of this patent is extended or adjusted under 35 U.S.C. 154(b) by 309 days.

(21) Appl. No.: 13/365,143

(22) Filed: Feb. 2, 2012

(65) Prior Publication Data

US 2013/0093108 A1    Apr. 18, 2013

Related U.S. Application Data

(60) Provisional application No. 61/439,618, filed on Feb. 4, 2011.

(51) Int. Cl.
*B01F 3/04*     (2006.01)
*A61L 9/12*     (2006.01)
*A61L 9/03*     (2006.01)

(52) U.S. Cl.
CPC ............... *A61L 9/122* (2013.01); *A61L 9/127* (2013.01); *A61L 9/032* (2013.01); *Y10S 261/88* (2013.01); *Y10S 261/89* (2013.01)
USPC ...... 261/30; 261/100; 261/142; 261/DIG. 88; 261/DIG. 89; 422/124; 239/58; 239/59

(58) Field of Classification Search
USPC ............... 239/58, 59; 422/124; 261/30, 100, 261/DIG. 88, DIG. 89
See application file for complete search history.

(56) References Cited

U.S. PATENT DOCUMENTS

| 5,704,832 A | * | 1/1998 | Borrell ........................ 454/157 |
| 5,935,526 A | * | 8/1999 | Moore ......................... 422/124 |
| 2003/0038133 A1 | * | 2/2003 | Liu ............................. 220/253 |

* cited by examiner

*Primary Examiner* — Robert A Hopkins
(74) *Attorney, Agent, or Firm* — McNair Law Firm, P.A.; Douglas W. Kim

(57) ABSTRACT

This application is directed to a fragrance dispenser attachably connected to a fan comprising: a housing having openings defined in the housing; a fragrance reservoir included in the housing for receiving a fragrance medium containing a fragrance; a cover operably associated with the opening for restricting airflow into the fragrance reservoir; and, a cover actuator operably connected to the cover having an open position allowing airflow into and out of the fragrance reservoir for dispensing a fragrance and a closed position for restricting airflow into and out of the fragrance reservoir.

19 Claims, 18 Drawing Sheets

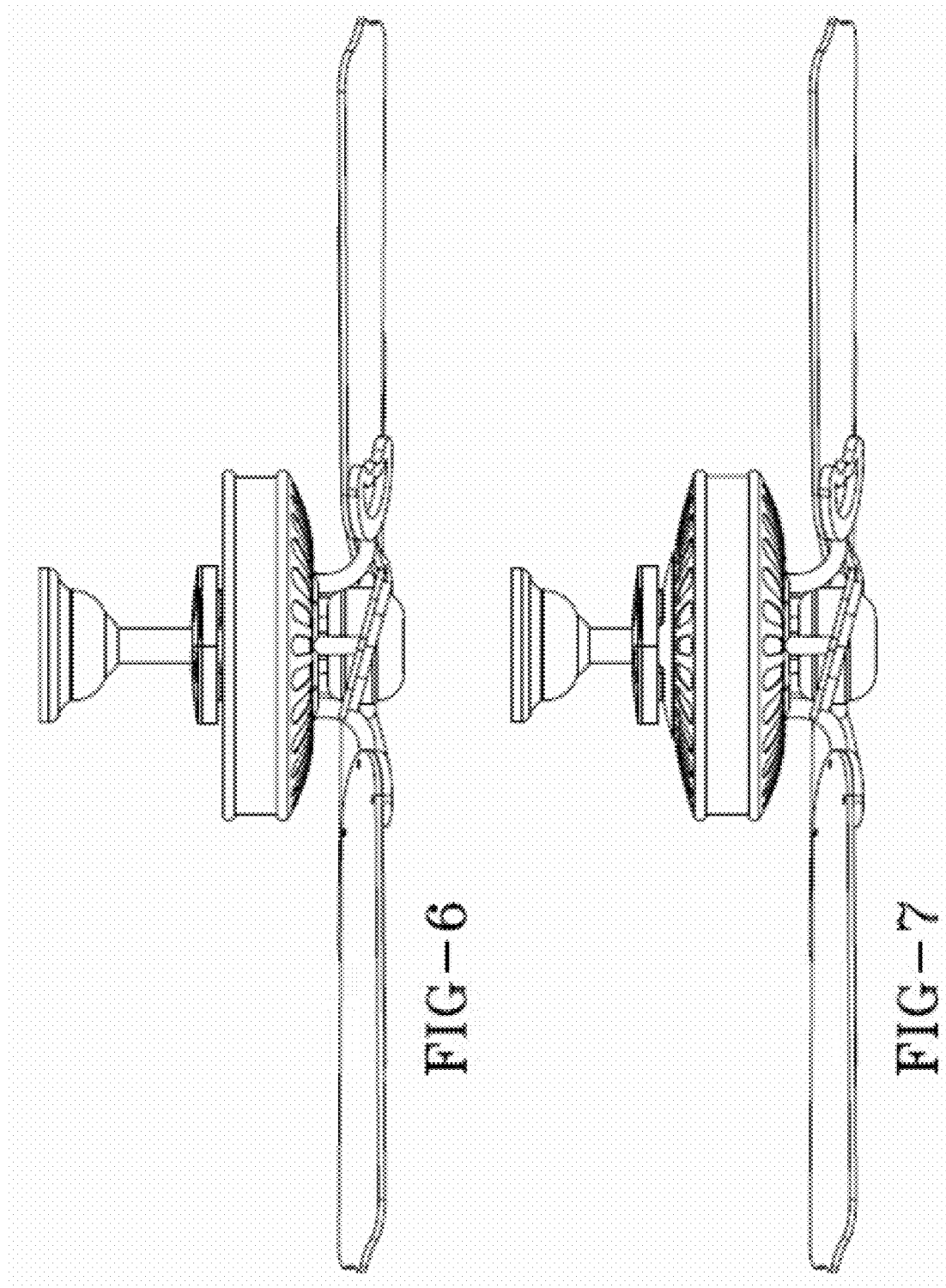

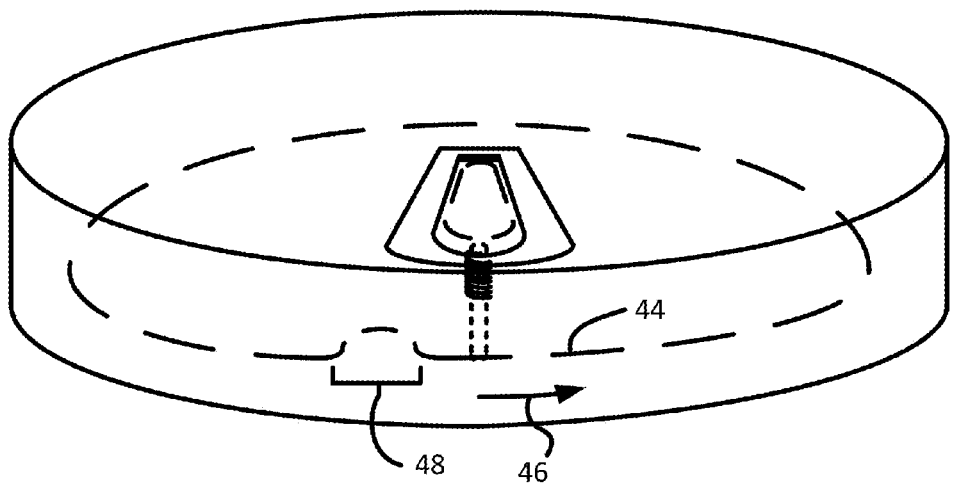
Fig 16
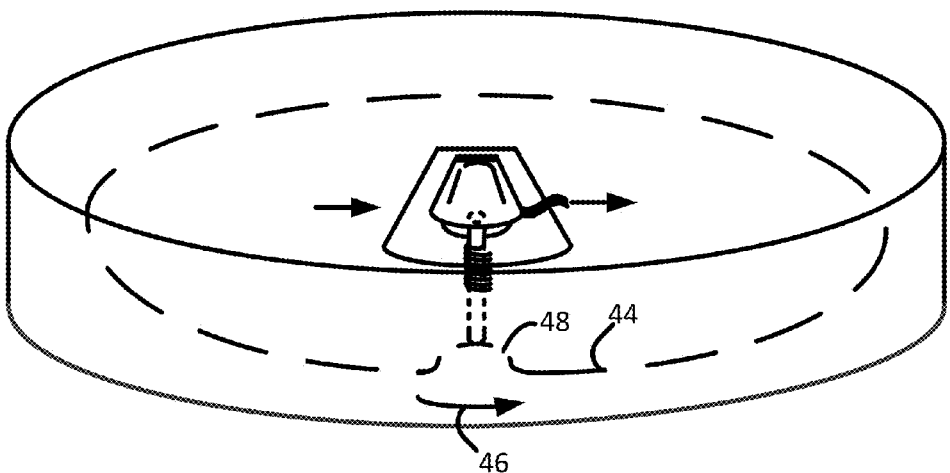
Fig 17
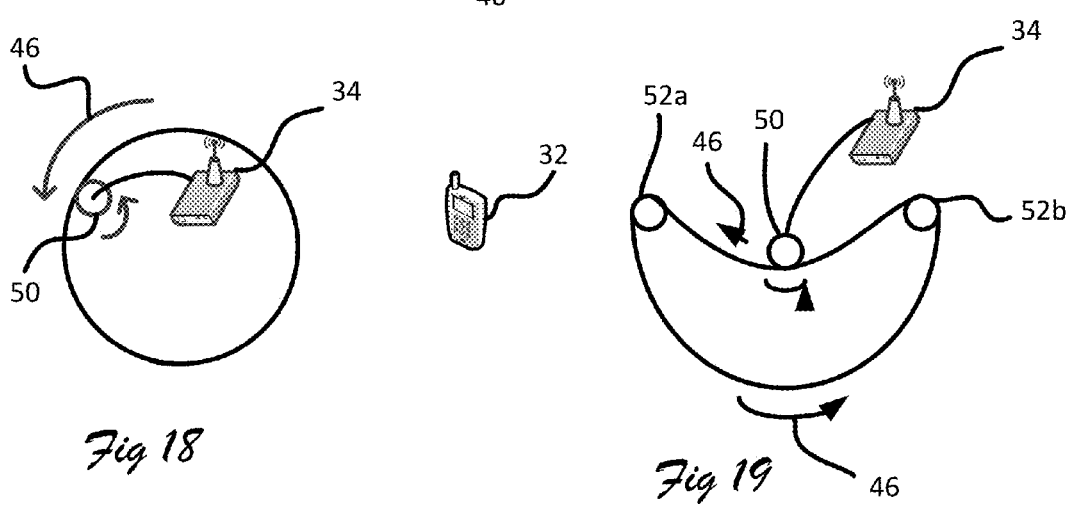
Fig 18
Fig 19

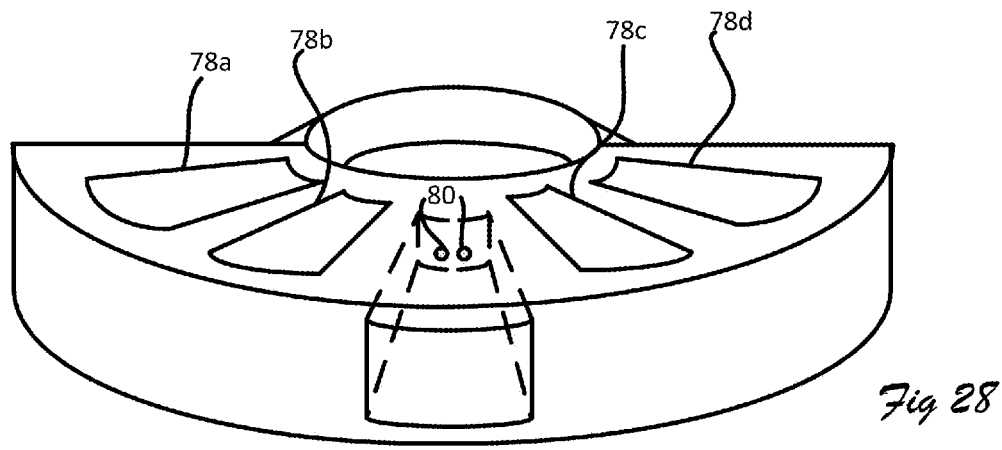
Fig 28
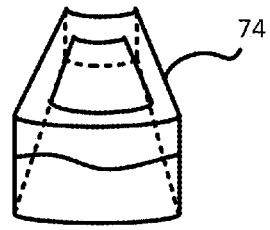
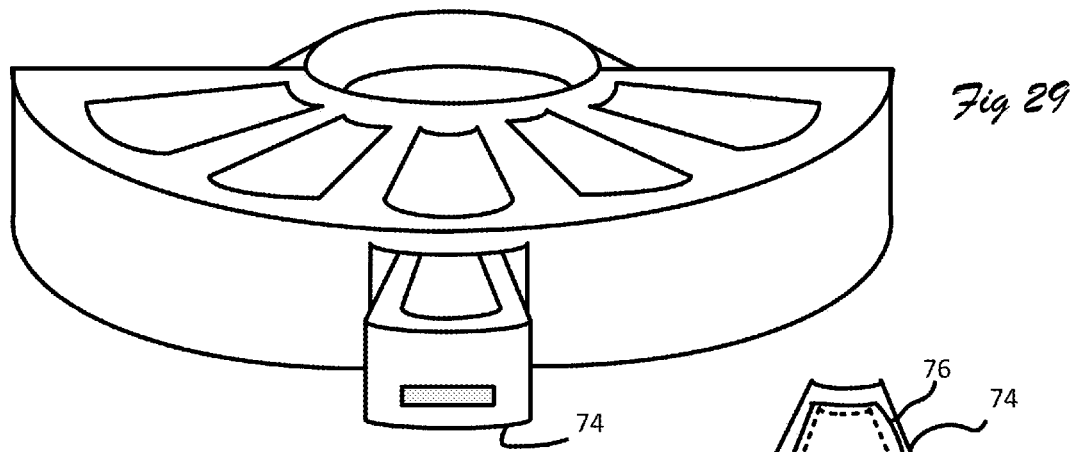
Fig 29
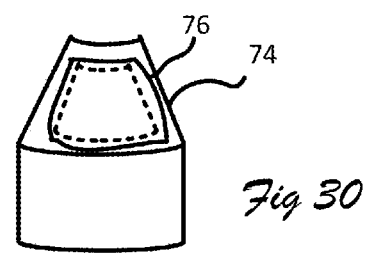
Fig 30

APPARATUS FOR DISTRIBUTING A FRAGRANCE USING A FAN

CLAIM OF PRIORITY

This application claims priority on U.S. Provisional Patent Application Ser. No. 61/439,618 filed Feb. 4, 2011.

FIELD OF THE INVENTION

This invention is directed to an apparatus for distributing fragrances using a fan, and more particularly, to an apparatus having multiple fragrances that can be selected by a user for distribution.

BACKGROUND OF THE INVENTION

There is a large market for various products used to mask and control unwanted odors in homes and work placed, or to enhance the air in a home or work place. Such products typically include air freshener sprays, blocks, electrically operated scent dispensers, candles, wicks, potpourri and the like. With all of these products, a number of drawbacks exist. With sprays, it is necessary to dispense the spray by hand in each room or area where the odor control is desired. With wicks, blocks, plug-in devices and the like, a number of them must be placed throughout the space in which the odor control is desired in order to obtain the desired results. With all of these products, however, the benefits are relatively expensive and short-lived. Some attempts have been made to produce automatic dispensers that are activated on a predetermined schedule, or when an object comes in proximity to the freshening device. These attempts include incorporating the release of odor control scents into the air handling system of furnaces and air conditioning systems.

However, none of these prior attempts include the ability to select one of a multiple of fragrances remotely from a dispenser when such dispenser is located out of reach, such as when installed on a ceiling fan. It is advantageous to have a dispenser in close proximity to a ceiling fan so that the air movement generated by the normal operation of a ceiling fan helps dissipate the fragrance.

Therefore, it is an object of this invention to provide an apparatus that can be selected remotely and can be installed in close proximity to a ceiling fan.

SUMMARY OF THE INVENTION

The above objectives are accomplished according to the present invention by providing a fragrance dispenser attachably connected to a fan comprising: a housing having openings defined in the housing; a fragrance reservoir included in the housing for receiving a fragrance medium containing a fragrance; a cover operably associated with the opening for restricting airflow into the fragrance reservoir; and, a cover actuator operably connected to the cover having an open position allowing airflow into and out of the fragrance reservoir for dispensing a fragrance and a closed position for restricting airflow into and out of the fragrance reservoir.

DESCRIPTION OF THE DRAWINGS

The invention will be more readily understood from a reading of the following specification and by reference to the accompanying drawings forming a part thereof, wherein an example of the invention is shown and wherein:

FIG. 6 shows the fragrance dispenser of FIG. 1 mounted on top of a ceiling fan that has a flat upper surface.

FIG. 7 shows the fragrance dispenser of FIG. 1 mounted on top of a ceiling fan that has a convex upper surface.

FIGS. 16 and 17 are a perspective views of the invention;

FIGS. 18 and 19 are schematics of the invention; and,

FIGS. 20 through 30 are perspective views of portions of the invention.

DESCRIPTION OF A PREFERRED EMBODIMENT

Referring now in more detail to the drawings, the invention will now be described in more detail.

A first embodiment of a fragrance dispenser for mounting to the top of a ceiling fan is shown in FIGS. 1-7. This first embodiment provides a fragrance dispenser that can be mounted to the top of a ceiling fan that has been previously installed in a structure, or can be incorporated into the original manufacture of a ceiling fan.

The fragrance dispenser comprises a housing that is a pair of complementary semi-circular housing members. Each of the semi-circular housing members has a removable top with a number of ventilation openings through the top. Each of the semi-circular housing members also has a bottom with a number of ventilation surfaces through the bottom. In the embodiment illustrated, the bottom is integral with a sidewall of the semi-circular housing member, but it is understood that the bottom may be a separate component that is fixed to the sidewall. The sidewall of the semi-circular housing member has a curved portion and a flat portion. The flat portion of the sidewall has a semi-circular indentation. The semi-circular housing members cooperate in their operative configuration to provide a central circular opening for receiving the downrod of a ceiling fan. A downrod is a metal pipe used to suspend the fan from the ceiling and it extends from the mechanism used to mount the fan to a ceiling to a housing of the fan's electric motor. The top of the housing of the fan's electric motor may be flat, as shown in FIG. 6, or may be convex, as shown in FIG. 7.

In one embodiment, one semi-circular housing is provided and a bracket is connected to the housing for securing the invention to a ceiling fan. The bracket and semi-circular housing can be connected by screws, clips, snaps or the like.

Figure 1:
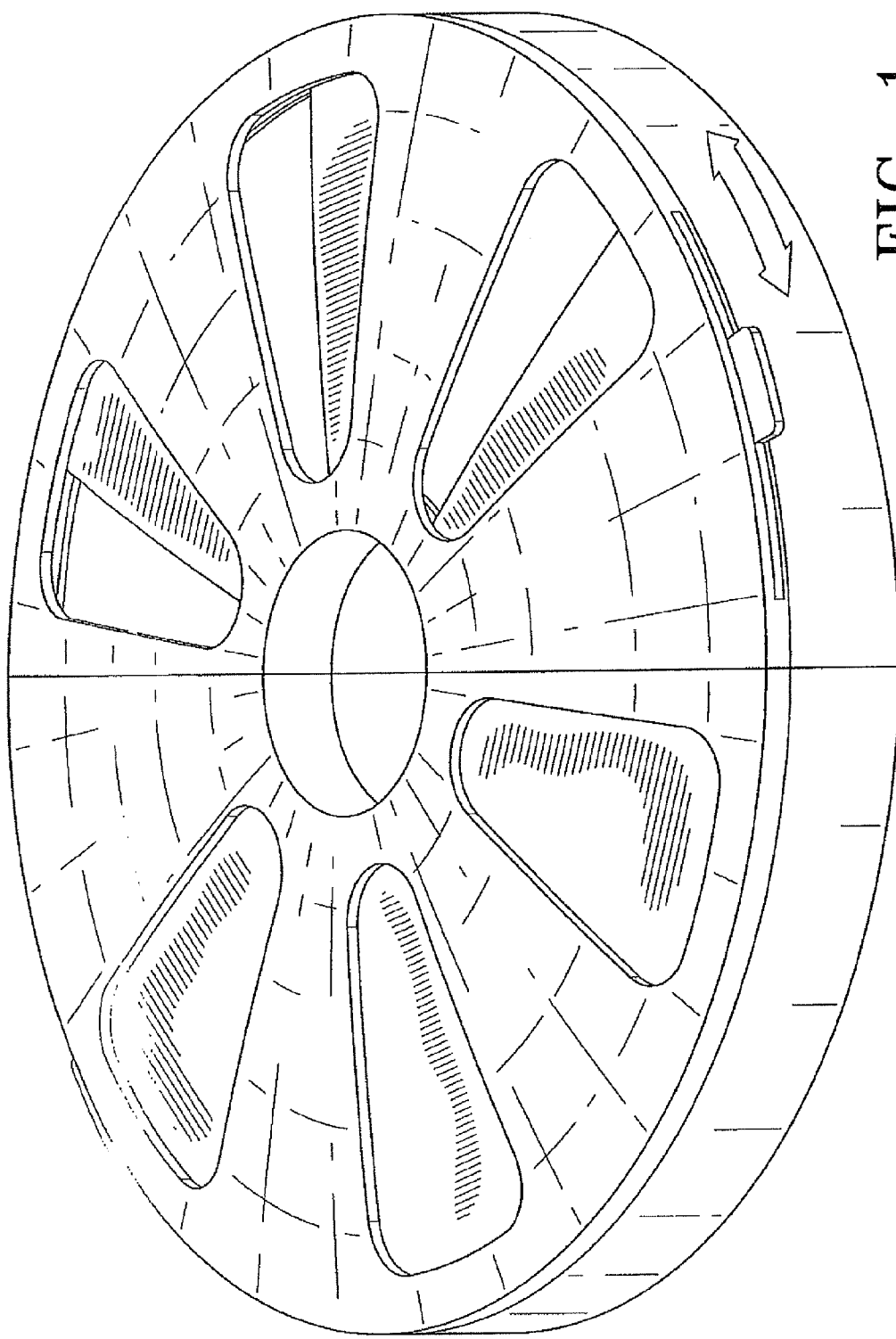
FIG. 1 is a perspective view showing the top of a fragrance dispenser according to a first embodiment designed to be mounted to the top of a ceiling fan.

In the embodiment shown there are three ventilation openings in the top of each of the semi-circular housing members, and as shown in FIG. 1 these openings are not spaced symmetrically. The shown locations of the ventilation openings in the top of the semi-circular housing members are selected to be coordinated with a shutter that is used to open and close the ventilation openings. The ventilation openings in the bottom of the semi-circular housing members are not closable, that is the ventilation openings in the bottom of the semi-circular housing members are always open.

Figure 2:
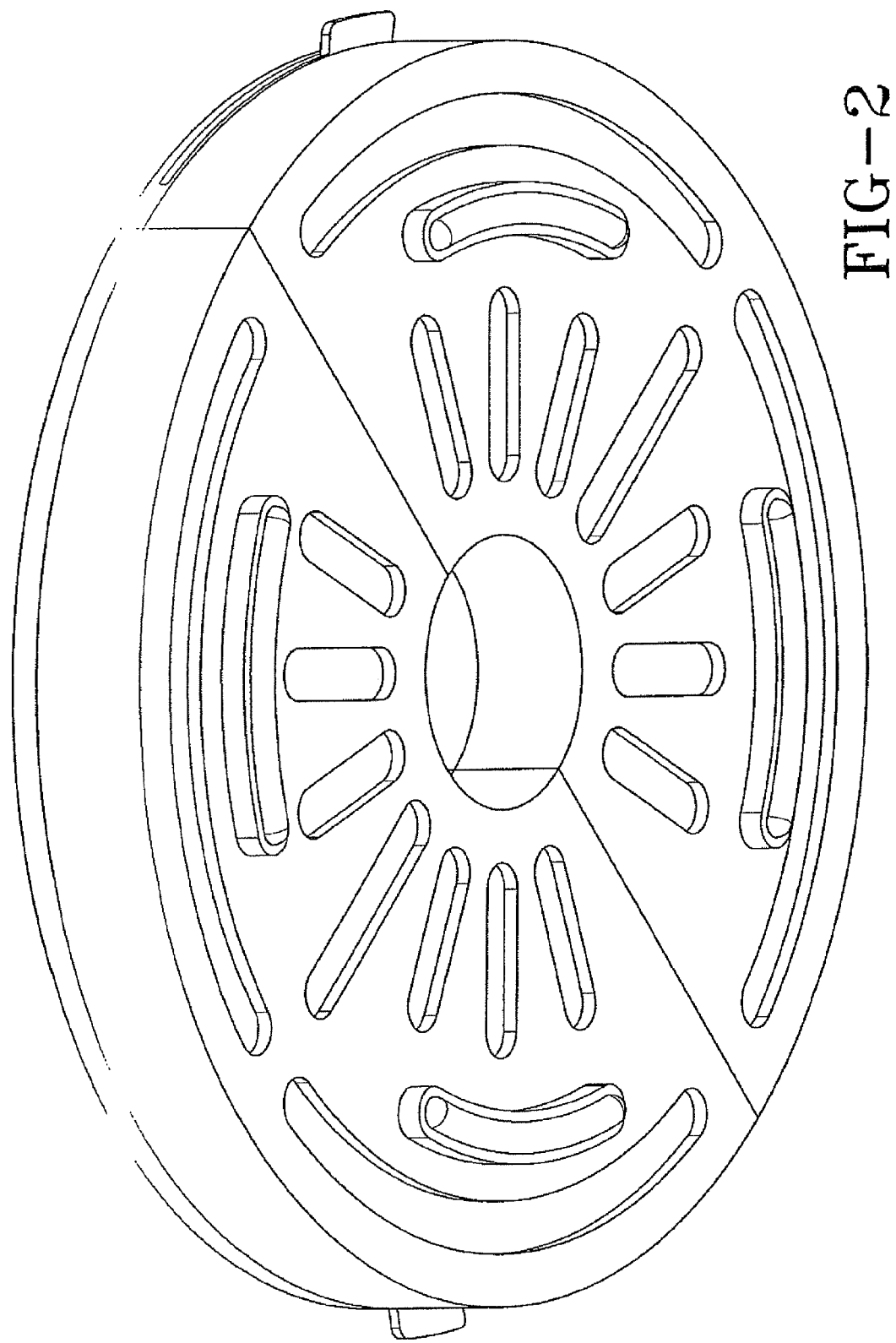
FIG. 2 is a perspective view showing the bottom of the fragrance dispenser of FIG. 1.

As shown in FIG. 2, the bottom of each semi-circular housing member has two sets of discontinuous arcuate pads projecting therefrom. Each set of arcuate pads is located between the vent openings and the sidewall of the semi-circular housing member, but at different distances from the sidewall. That is, the sets of arcuate pads are located at different distances from a center point of the arc of the sidewall of the semi-circular housing member measured radially with respect to the center point. It is understood that while in this example the pads are arcuate, they could instead be a series of circular pads. Preferably, the heights of all of the pads with respect to the bottom of the semi-circular housing member are the same. It is understood that while in this example the pads are arcuate, they could instead be a series of circular pads. If the fragrance dispenser of this embodiment is mounted on top of a fan motor housing having a flat top, as in FIG. 6, all of the pads will rest on the top of the fan motor housing. If the fragrance dispenser of this embodiment is mounted on top of a fan motor housing having a convex top, as in FIG. 7, only the radially innermost pads will rest on the top of the fan motor housing. It is understood that the locations and heights of the pads can be varied to enhance installation of a fragrance dispenser with a variety of ceiling fans.

Figure 3:
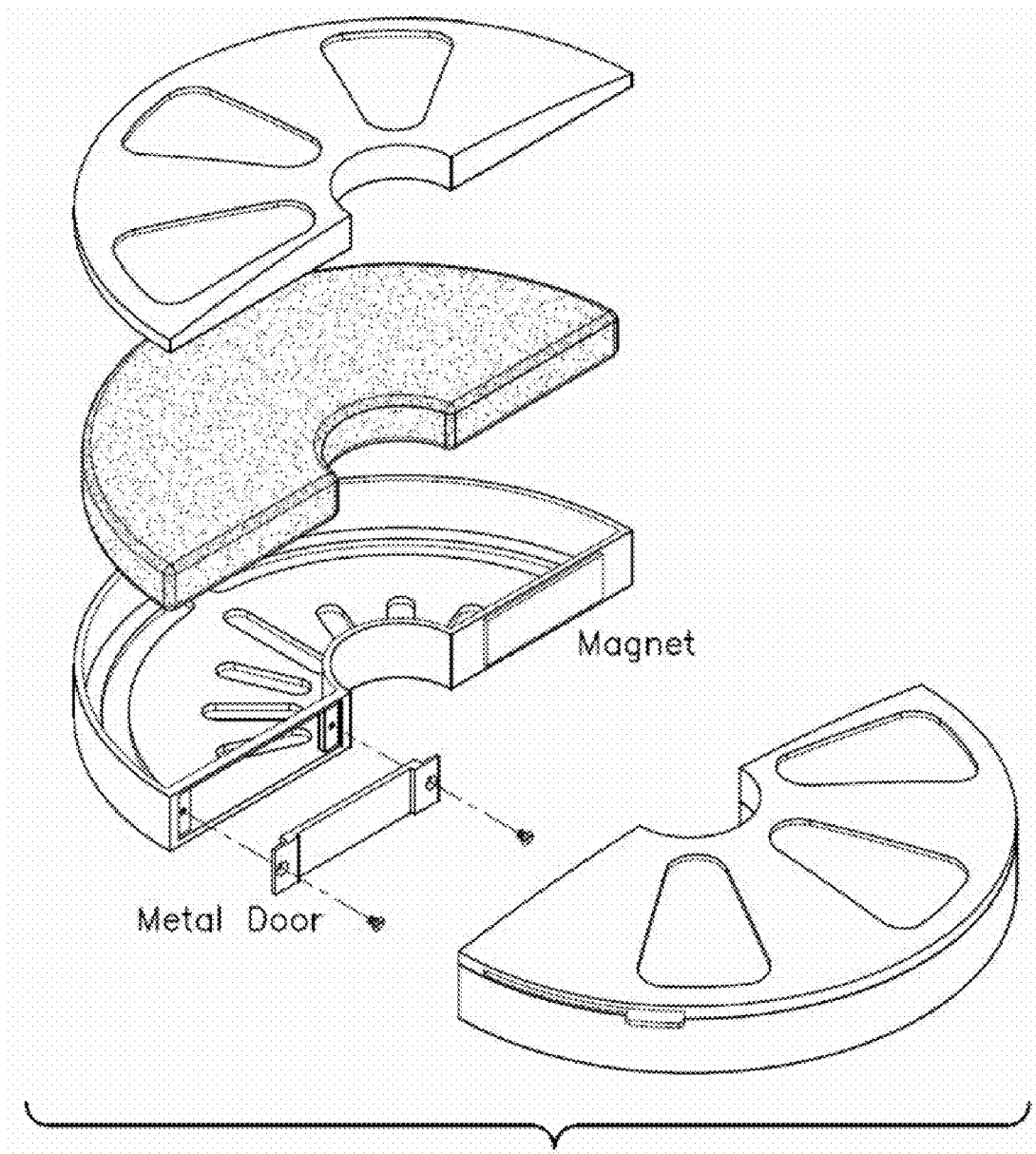
FIG. 3 is an exploded view of the fragrance dispenser of FIG. 1.

The complementary semi-circular housing members are fixed to one another on the top of a motor housing of a ceiling fan with the downrod received in the central circular opening of the assembled fragrance dispenser. The two semi-circular housing members may be secured to one another in an operative location using any suitable means, including magnets, threaded fasteners, screws, clips, and snap fit fastener arrangements. In FIG. 3 one of the semi-circular housing members is provided with magnets that mate with ferrous components on the other semi-circular housing member.

A fragrance releasing element is located in each semi-circular housing member. The fragrance releasing element may, for example, be a fibrous pad that serves as a permeable substrate to which a fragrant material is applied, or a porous bag that contains fragrance releasing spheres, granules or the like. The fragrances released from each of the semi-circular housing members can be the same or, if desired, the fragrances released from the semi-circular housing members may be different. If the shutters are both moved to a position such that the vent openings in the tops of the housing members are closed, only a minimal amount of fragrance may escape from the fragrance dispenser. However, when the shutters are both moved to positions such that the vent openings in the top of the housing members are fully opened, a maximum amount of fragrance escapes from the fragrance dispenser when the fan is operating. The amount of fragrance released may be further varied by adjusting the openings of the vents using the shutters. In this first embodiment the shutters are operated manually.

A fragrance escaping from the vent openings of the fragrance dispenser will be distributed into the space where the associated ceiling fan is installed by the circulating air that is being moved by the rotating blades of the ceiling fan. While the space in which air is circulated by the fan is typically an interior space, such as a room, hallway or open area in a building, it is anticipated that the fragrance dispenser will also have utility with ceiling fans located in outdoor spaces like lanais. Furthermore, if the heights and arrangements of the pads on the bottom of the fragrance dispenser are properly dimensioned for mounting to the top of the motor housing of any particular ceiling fan to facilitate airflow between the bottom of the fragrance dispenser and the top of the motor housing, circulation of the fan blades will cause air to flow through the vent openings in the top of the fragrance dispenser into the housing members, then through the fragrance releasing elements, and then to exit the fragrance dispenser through the vent openings in the bottoms of the fragrance dispenser. If the direction of rotation of the fan blades is reversed the flow of air through the fragrance dispenser may also be reversed. Regardless of the direction of flow of air through the fragrance dispenser, the flow of air into an interior space by the ceiling fan will distribute the fragrance into the interior space.

Figure 11:
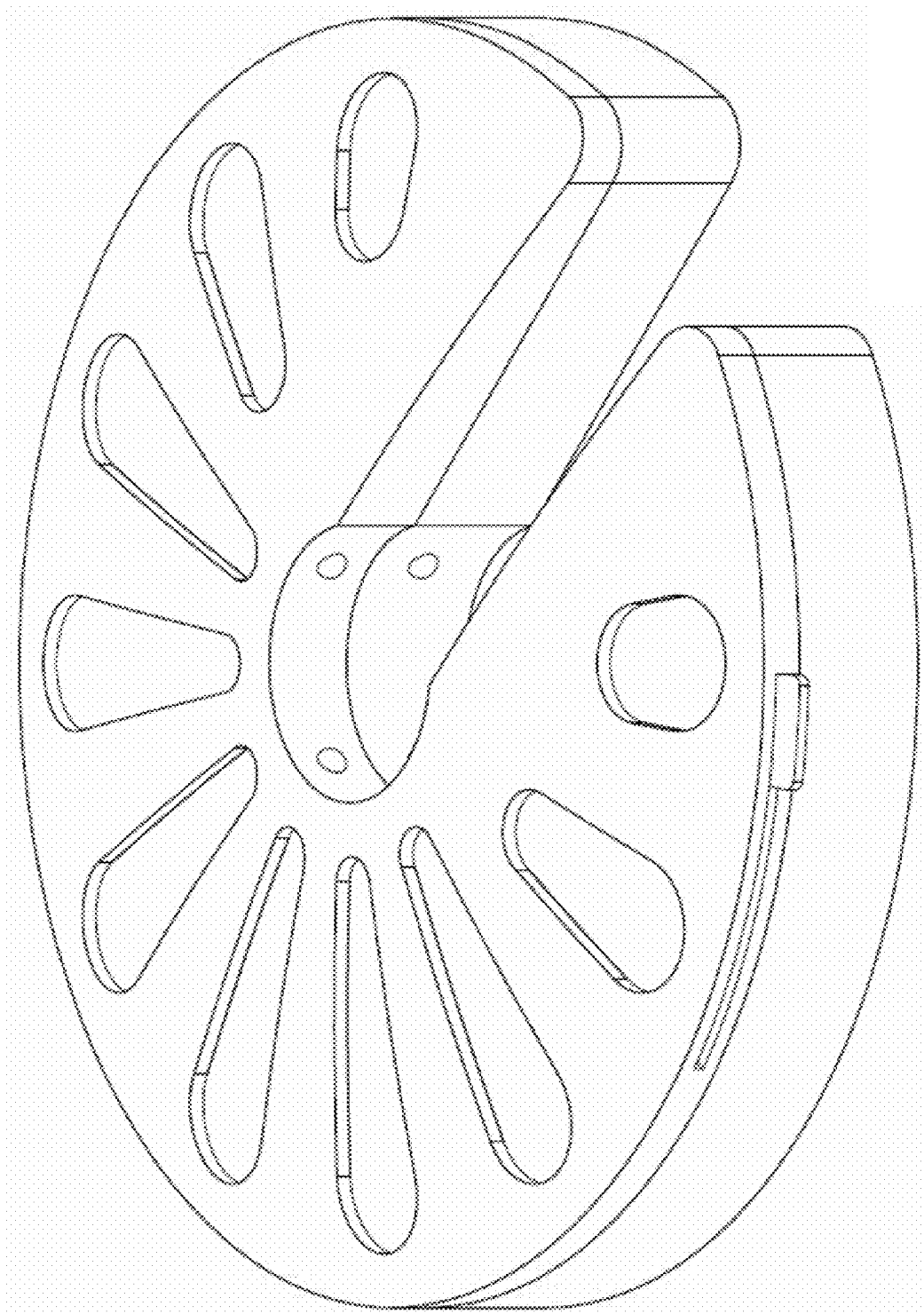
FIG. 11 is a perspective view of the fragrance dispenser according to a third embodiment designed to be mounted to the top of a ceiling fan.
Figure 12:
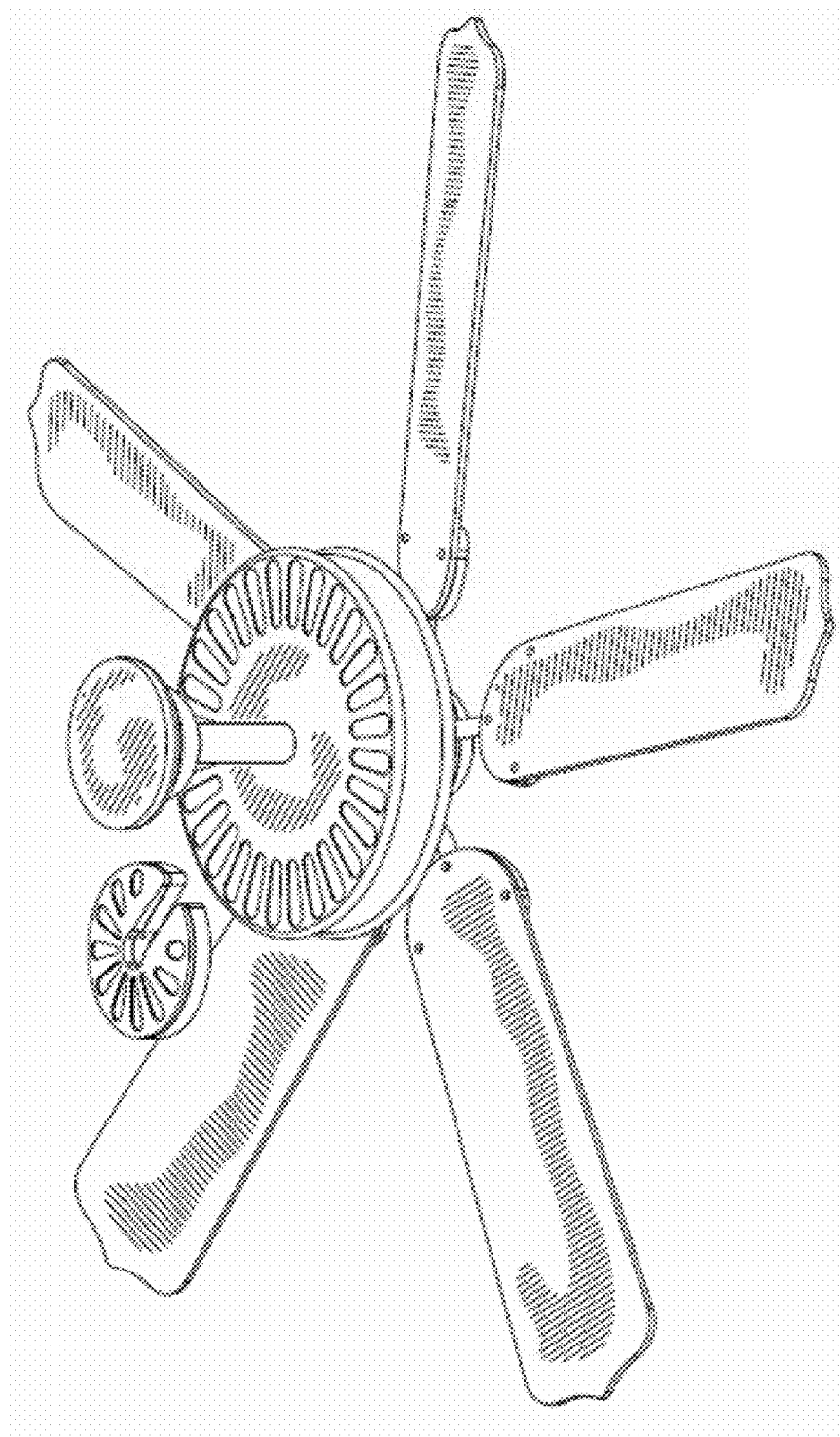
FIG. 12 is a perspective view of a fragrance dispenser according to a third embodiment designed to be mounted to the top of a ceiling fan.

In an alternative embodiment shown in FIGS. 11 and 12, a single housing member that is generally cylindrical, but having a channel that passes around the down rod of a ceiling fan to allow the down rod to be received in the open space at the center of the housing member. In all other respects, the second embodiment is like the first embodiment. The fragrance dispenser of the second embodiment is intended for mounting to a previously installed ceiling fan. After sliding the fragrance dispenser around the down rod of a ceiling fan the dispenser is fixed to the down rod by means for securing such as set screws.

Figure 4:
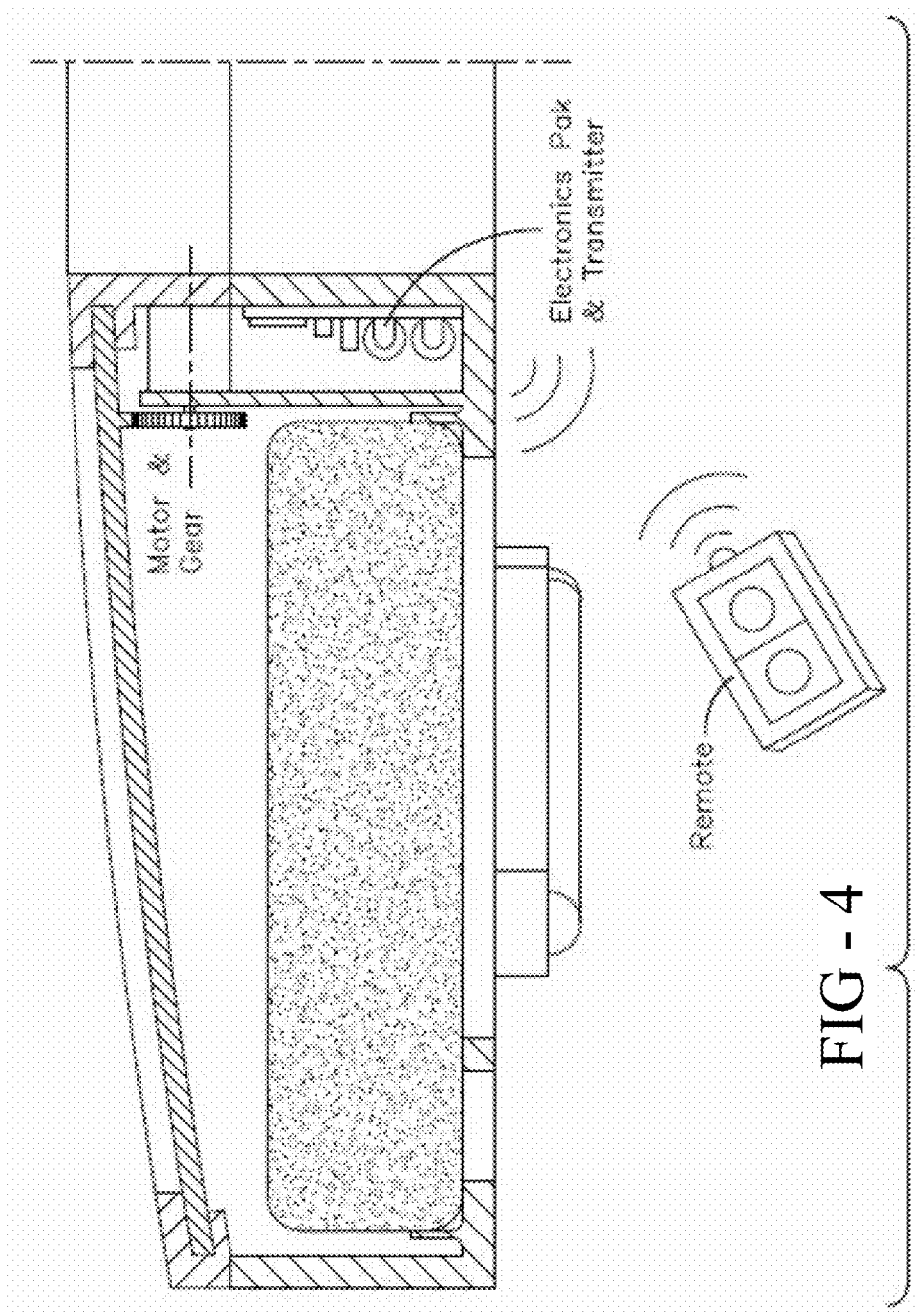
FIG. 4 is a cross-sectional view of the fragrance dispenser of FIG. 1 equipped with a remote controlled electric motor for opening and closing a shutter.
Figure 5:
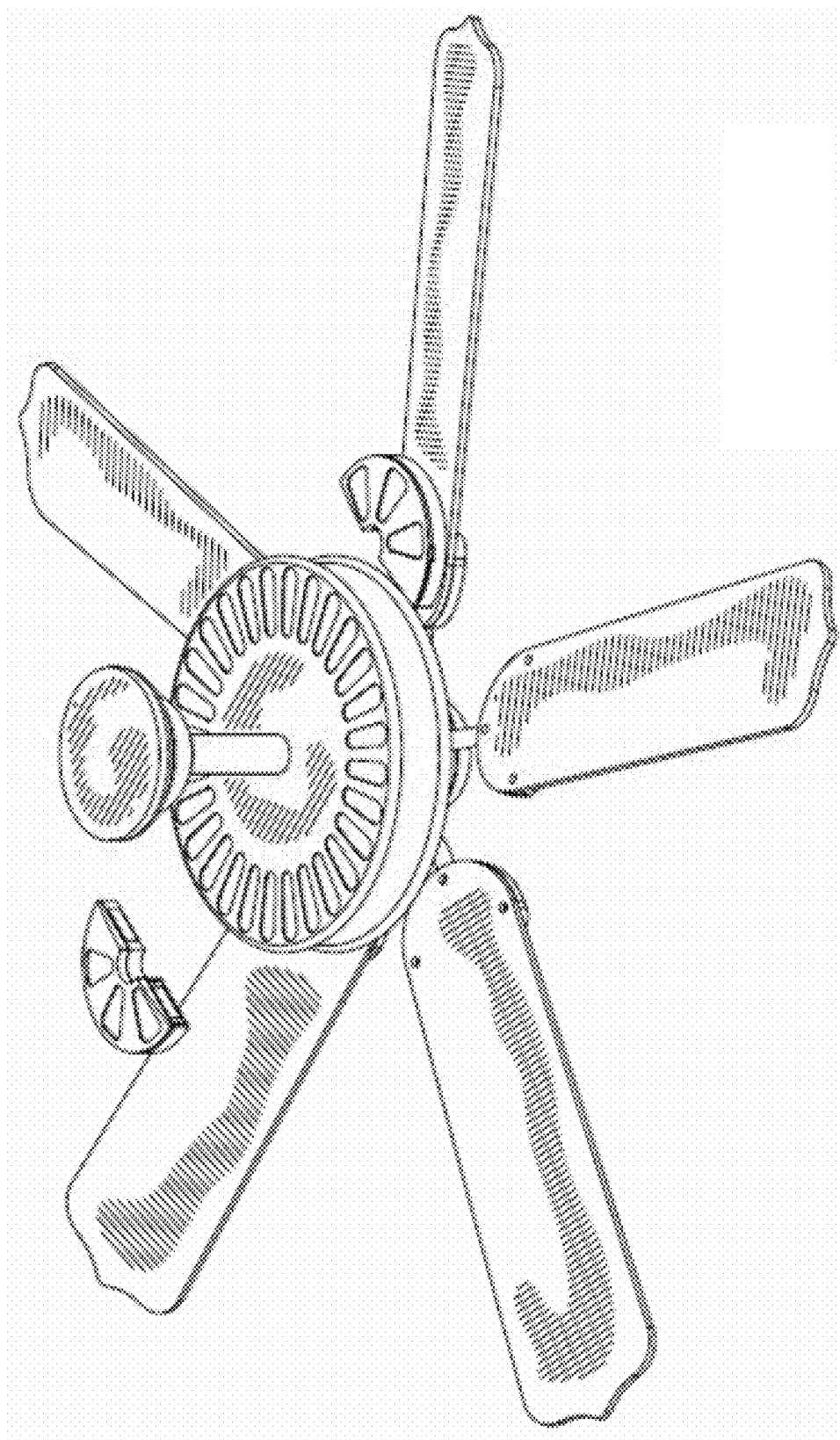
FIG. 5 shows the fragrance dispenser of FIG. 1 ready to be mounted on the top of a ceiling fan.

Ceiling fans may be located to be accessible easily in rooms with relatively low ceilings, but many ceiling fans are located in spaces with higher ceilings. In such a situation it may be desirable to have the shutter of a fragrance dispenser operable by an electric motor that is activated using a remote control, as shown in FIG. 4.

While the first two embodiments of a fragrance dispenser for use with a ceiling fan are designed to be retrofitted to a previously installed ceiling fan, a fragrance dispenser can also be installed as a part of the installation of a ceiling fan, and could either be sold separately or as a part of a ceiling fan kit. A fragrance dispenser of this third embodiment comprises a circular housing member having a top, a bottom, a circumferentially extending outer sidewall, and a circumferentially extending inner sidewall that surrounds a circular passage for receiving the down rod of a ceiling fan.

Figure 8:
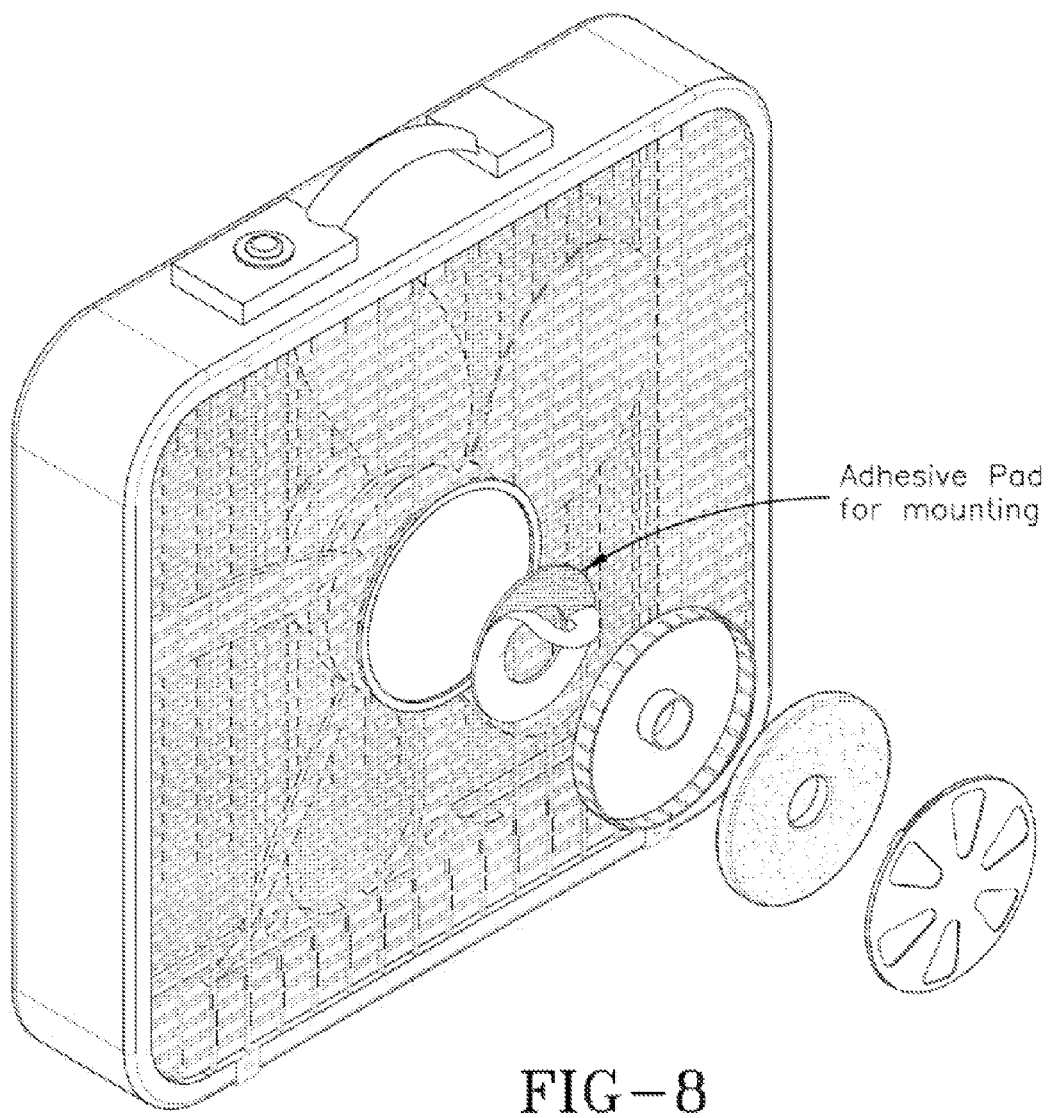
FIG. 8 is an exploded view of a fragrance dispenser according to a second embodiment for mounting on a box fan.
Figure 9:
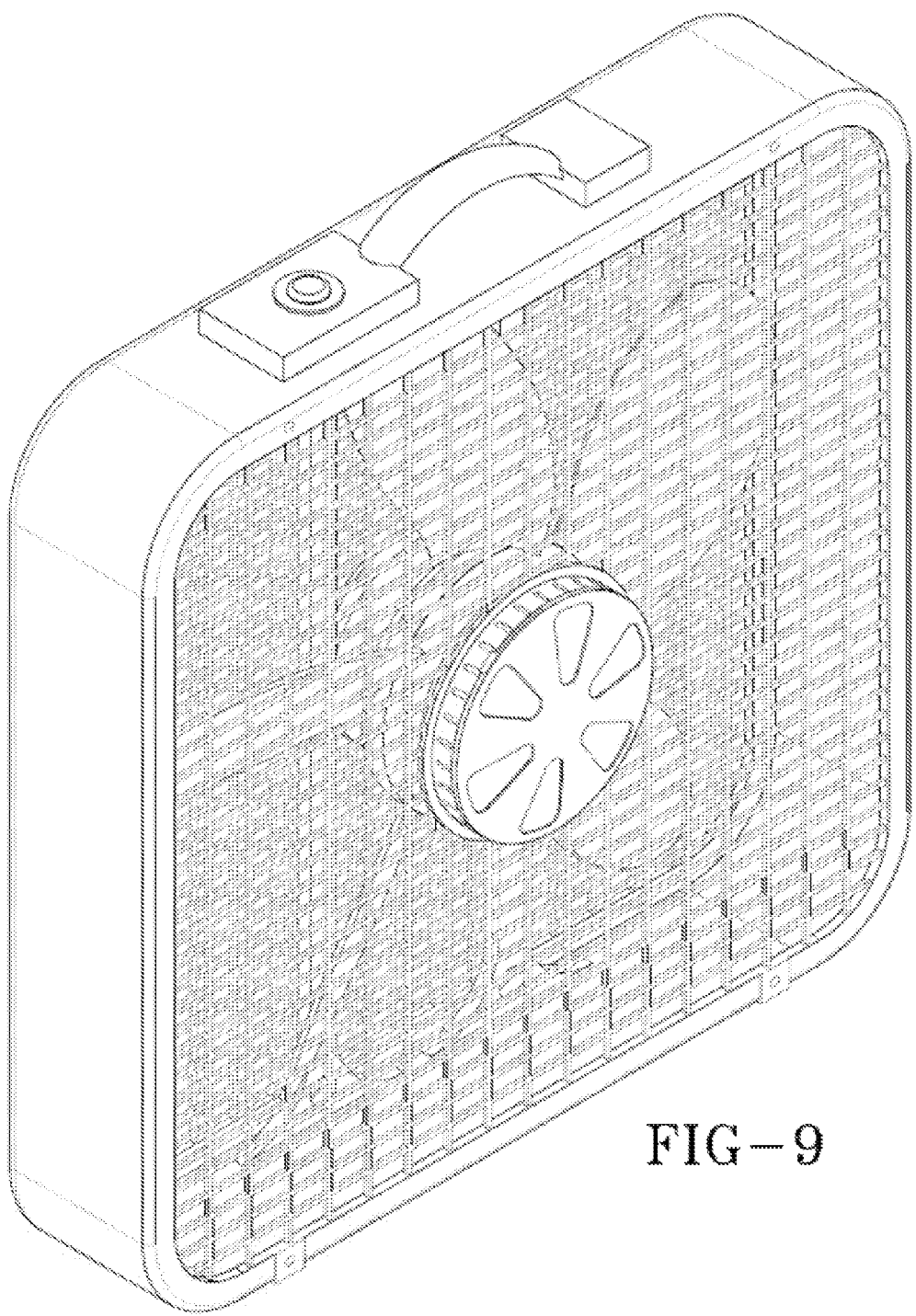
FIG. 9 is a perspective view of the fragrance dispenser of the second embodiment mounted on a box fan.

FIGS. 8 and 9 show a fragrance dispenser to be mounted to a box fan.

Figure 10:
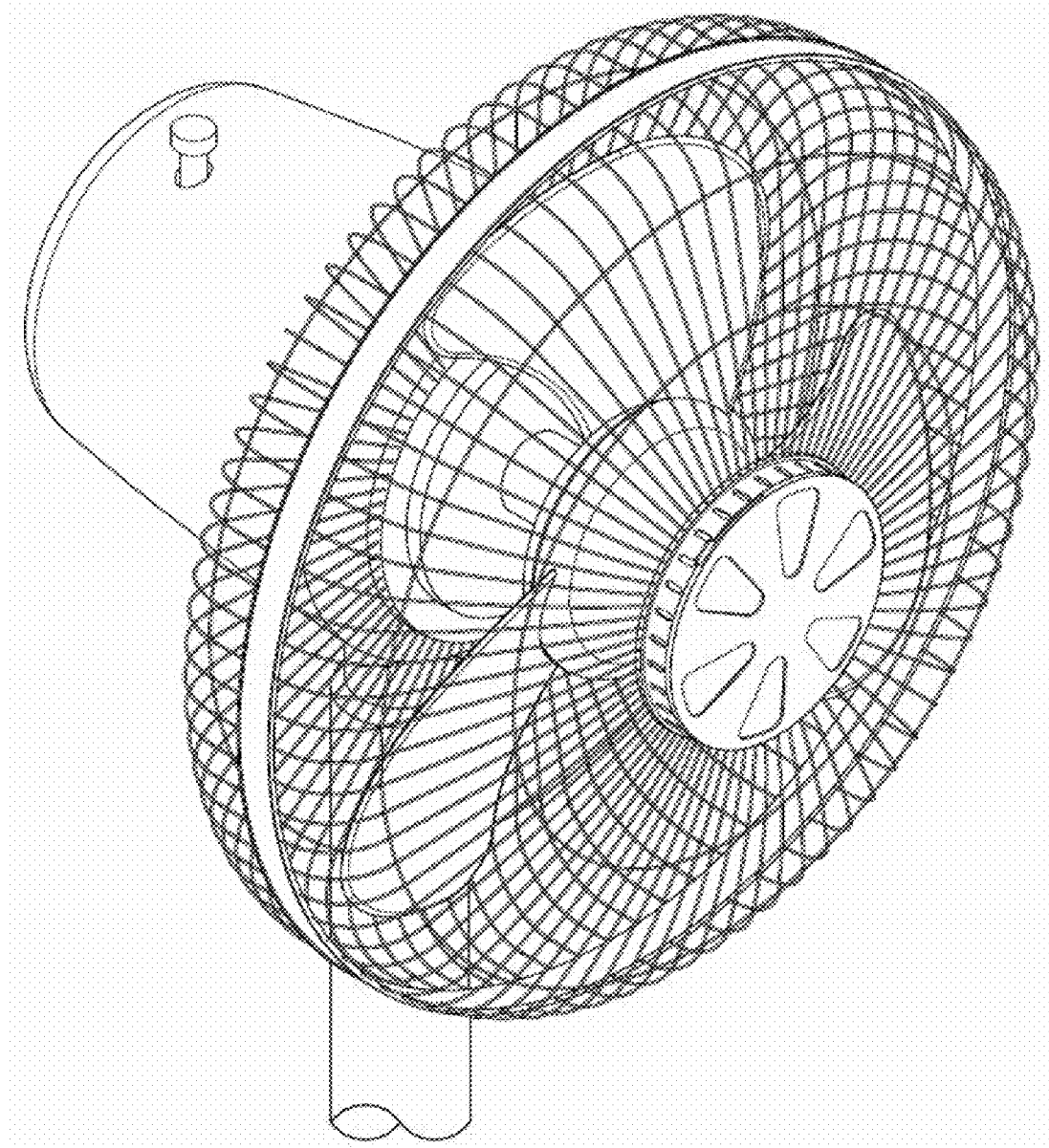
FIG. 10 is a perspective view of a fragrance dispenser according to the second embodiment for mounting on a pedestal fan.

FIG. 10 shows a fragrance dispenser to be mounted to a pedestal fan.

Figure 13:
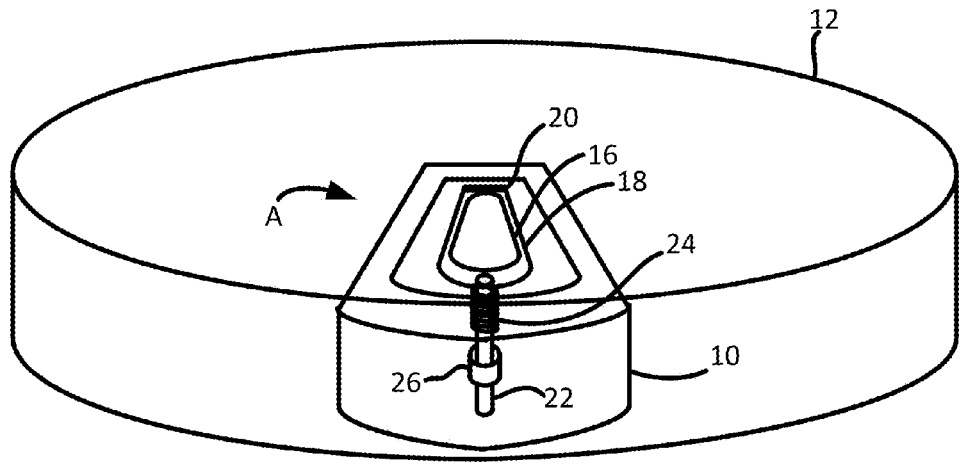
FIG. 13 is a perspective view of the invention.

Referring now to FIG. 13, another embodiment is described. A fragrance container 10 is carried by a housing 12. The container can receive fragrance pads, cloth, blocks, solid, liquids, or other fragrance dispensing material through opening 16 after lifting cover 18. Cover 18 can be hingably connected by cover connection point 20 to the housing. The cover can have an opening rod 22 carried by the cover or operably contacting the cover. A spring 24 can be carried by the opening rod and biased downward. The cover, in a closed position (shown as A) rests on opening 16 and seals the fragrance container so that it is airtight, or nearly airtight, effectively restricting airflow into and out of the fragrance container.

An electromagnet 26 connected to a power supply can, when energized, apply a force upward on the opening rod and push the cover upward away from the opening of the fragrance container.

Figure 14:
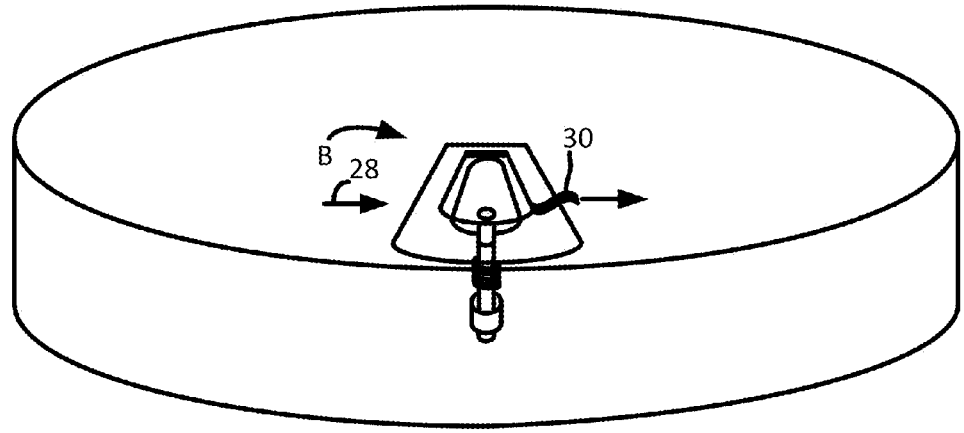
FIG. 14 is a perspective views of the invention.

Referring to FIG. 14, the open position C (shown as B) allows airflow 28 to carry fragrance out of the fragrance container and into the surrounding air. When the ceiling fan is operational, the fragrance flows in the resulting air streams.

Figure 15:
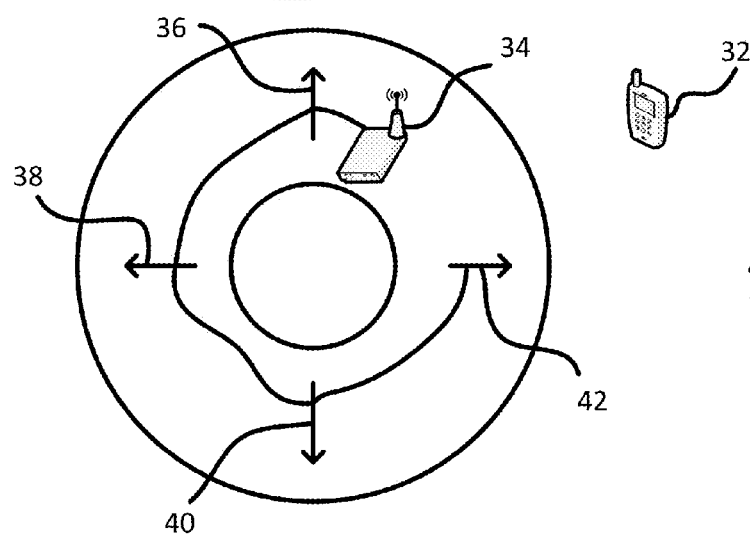
FIG. 15 is a schematic of the invention.

Referring to FIG. 15, a top view of the invention is shown. A remote control 32 is releasably in communication with activator 34. The activator can be battery powered or can be connected to the power supply of the fan or the home electrical wiring system. When the activator receives a signal from the remote, the activator steps through several states that include each fragrance container electromagnet and an all closed state. For example, in the all closed state no electromagnet is energized and each of the covers are closed. When the actuator receives a signal, the activator energizes the first electromagnet 36 so that the associated cover is open and the fragrance in the associated fragrance container is released into the surrounding air. In one embodiment, a visual indicator in proximity to the fragrance container is illuminated to indicate which cover is open. In one embodiment, a visual indicator, such as a light or alphanumeric character, on the remote associated with the first cover is activated indicating the state of the activator.

When the next signal is received, the activator de-energizes the first electromagnet 36 and energizes the second electromagnetic 38. Therefore, the fragrance in the first fragrance container can no longer supply sufficient fragrance to effectively effect a room but the fragrance in the fragrance container associated with electromagnetic 38 can.

When the next signal is received, the electromagnetic 40 is energized and electromagnet 39 is de-energized. When the next signal is received, electromagnet 42 is energized opening the associated cover. When the next signal is received the actuator de-energizes electromagnet 42 so that all covers are closed.

In this embodiment, there is no opening so that the covers to the fragrance containers control whether fragrance is released or not. In one embodiment, the activator can include states that are combinations of fragrances in fragrance containers. For example, one state may be that electromagnets 34 and 38 are energized allowing the fragrances of both fragrance containers to be distributed into the room.

Referring to FIG. 16, another embodiment is shown. An actuator member 44 travels in a direction shown as 46. A contact 48 is included in the actuating member. The contact can be of a rigid construction while the remainder of the actuating members can be flexible, such as with a string belt, chain, strap and the like. When the contact and opening rod are not aligned as in FIG. 17, the cover is closed due to the spring. In one embodiment, the cover is biased to the closed position due to the weight of the cover.

When the contact and opening rod are aligned, the contact, being higher in elevation, pulls the opening rod upwards thereby opening the cover. When the contact is advanced in a direction 46 so that the contact and opening rod are no longer aligned, the cover is closed.

Referring to FIG. 18, a drive member 50 is in electronic communication with actuator 34. When actuator 34 receives a signal from remote 32, the actuator causes the drive to advance in a direction shown as 46 thereby being the contact from opening rod to opening rod allowing each fragrance container to be opened while closing the proceeding fragrance container. Further, the drive member can locate the contact between opening rods so that all covers for all fragrance containers are closed.

Referring to FIG. 19, the actuating member need not take any particular shape as idlers 52c and 52b can direct the actuating member along a predetermined path. In this embodiment, drive 50 moves the actuating member, and contact, along a path 46 with predetermined stops so that the contact is aligned with the opening rods in series and, in one embodiment, between opening rods.

Figure 20:
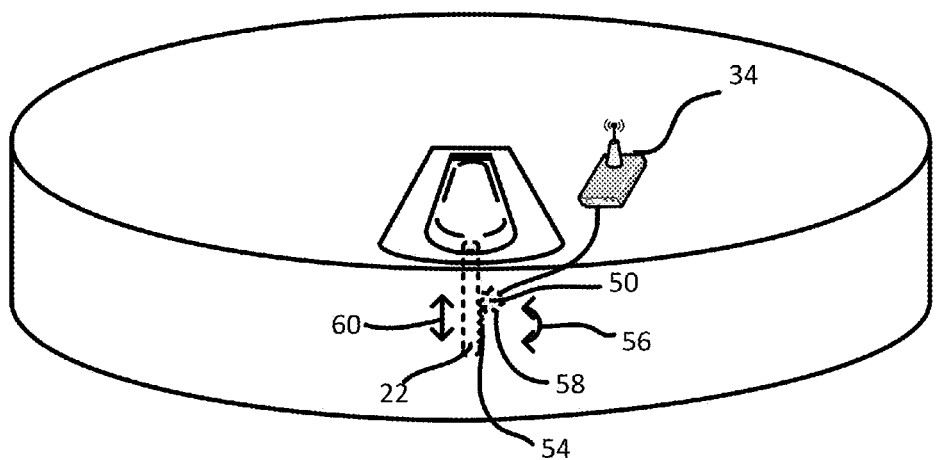
Figure 21:
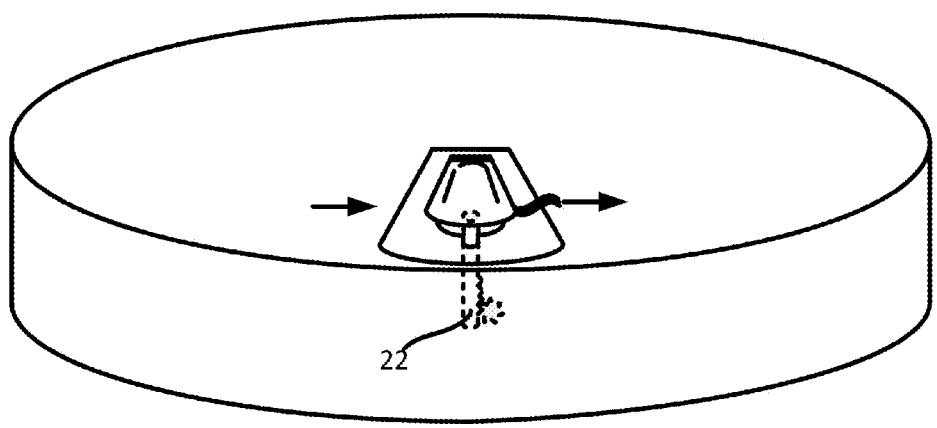

Referring to FIGS. 20 and 21, another embodiment is shown. Opening rod includes a set of teeth 54 operably connected with drive 50. Actuator 34 is operably connected with the drive and can rotate in a direction shown as 56. When the actuator operates the drive to rotate a gear 58, the opening rod can be moved in a direction shown as 60, thereby opening and closing cover 18.

Figure 22:
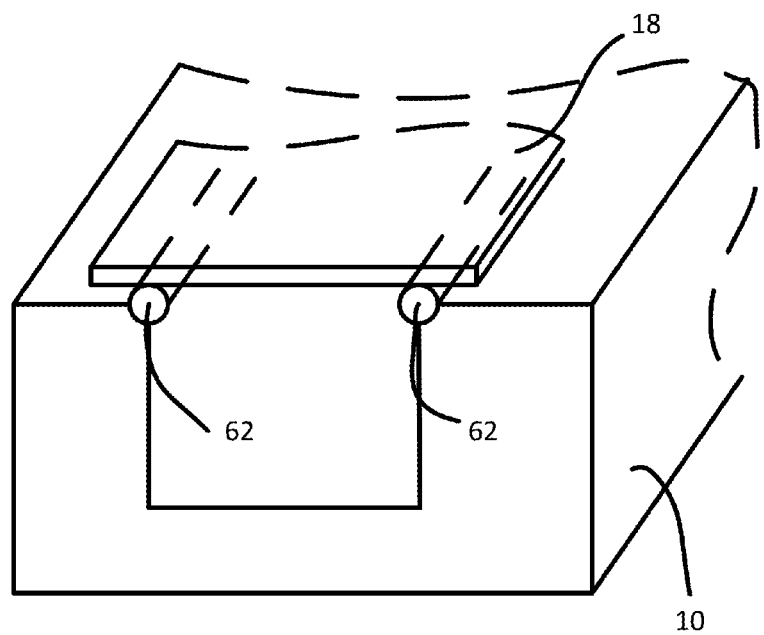
Figure 23:
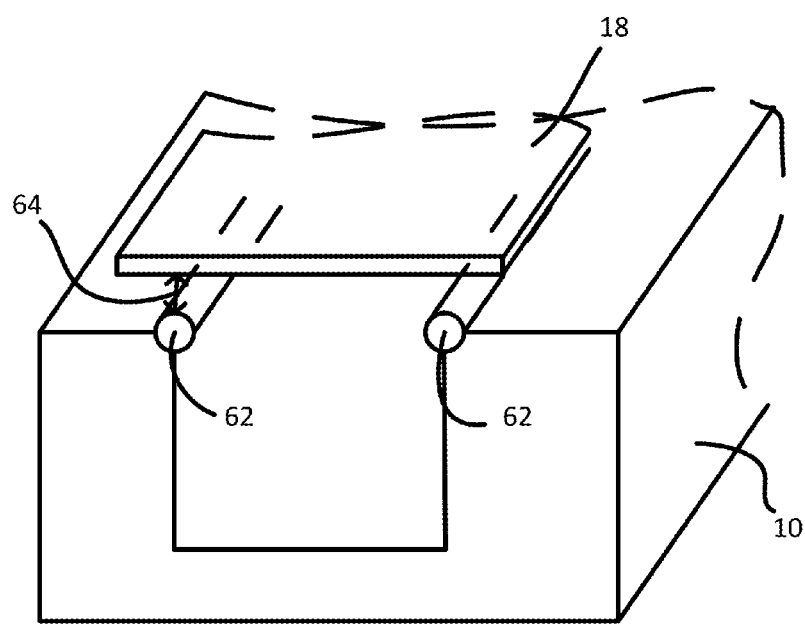

Referring to FIGS. 22 and 23 (cross-sections), one embodiment of the cover is shown. Fragrance container carries cover 18. Cover 18 is biased in the closed position and when closed, contacts seal 62. When cover 18 contacts seal 62, on o-ring for example, airflow is restricted so that insufficient fragrance is released into the room. When cover 18 is opened, space 64 is created allowing airflow 28 to enter the fluid container and fragrance 30 to exit.

Figure 24:
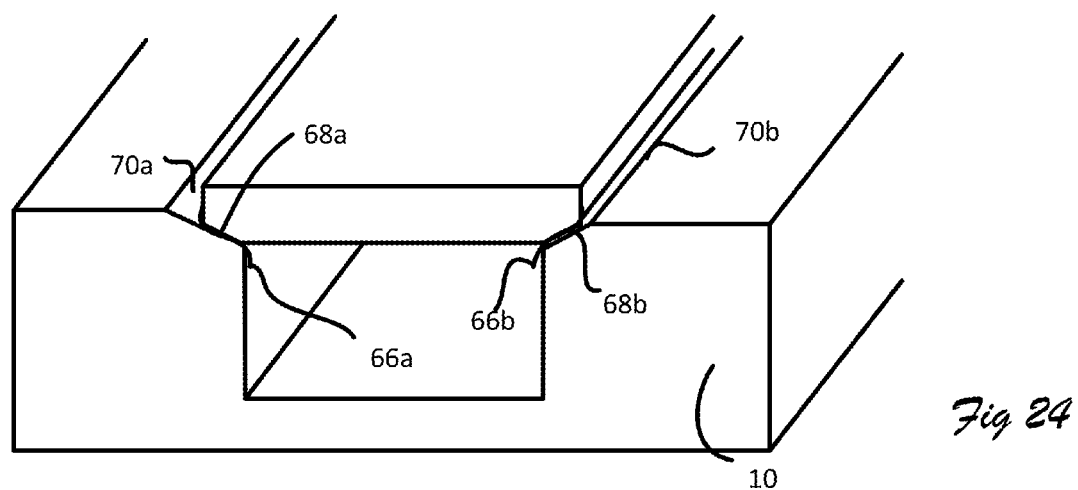
Figure 25:
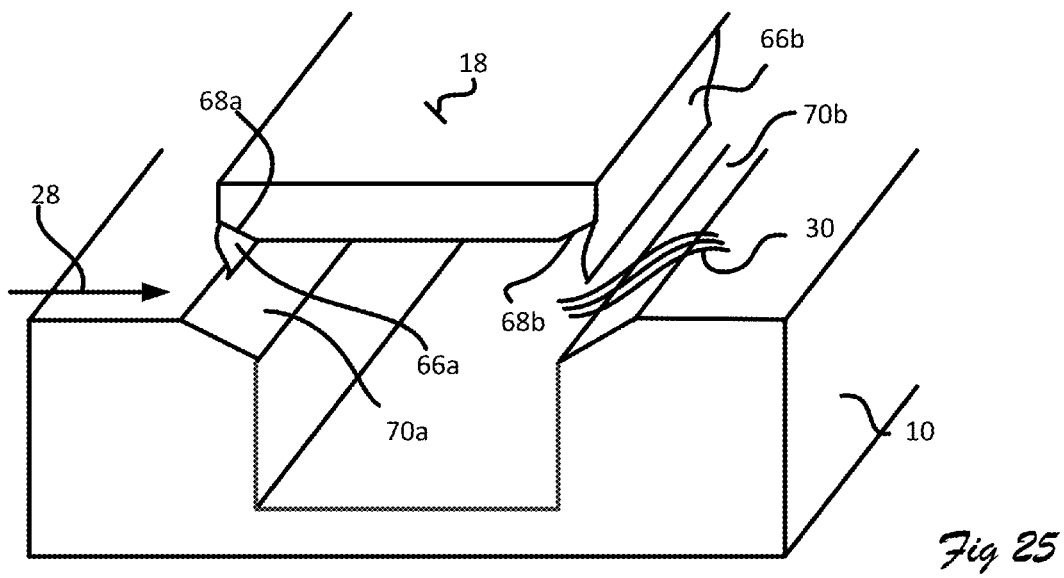

Referring to FIGS. 24 and 25, another embodiment is shown. Skirt members 66a and 66b are carried by cover 18. In the closed position, the skirts are in contact with edges 68a and 68b of the cover respectively, as well as fragrance container edges 70a and 70b respectively, restricting airflow 28 allowing fragrance 30 to exit the fragrance container into the room.

Figure 26:
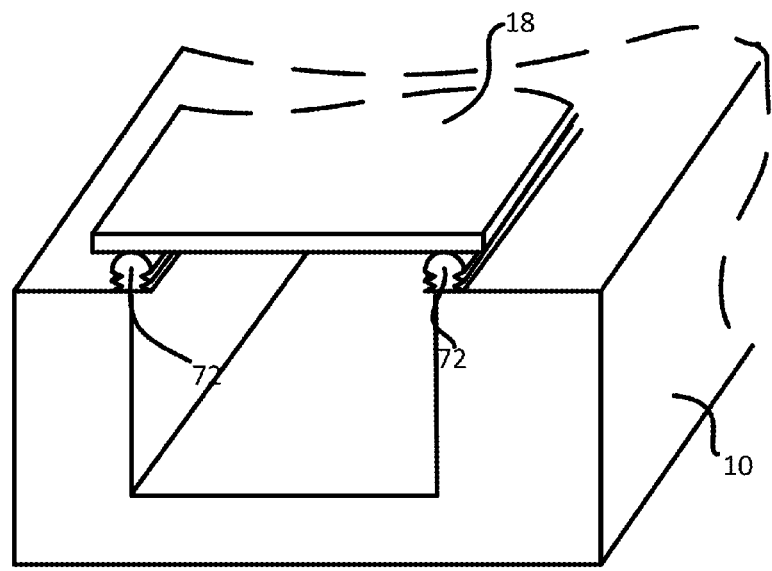
Figure 27:
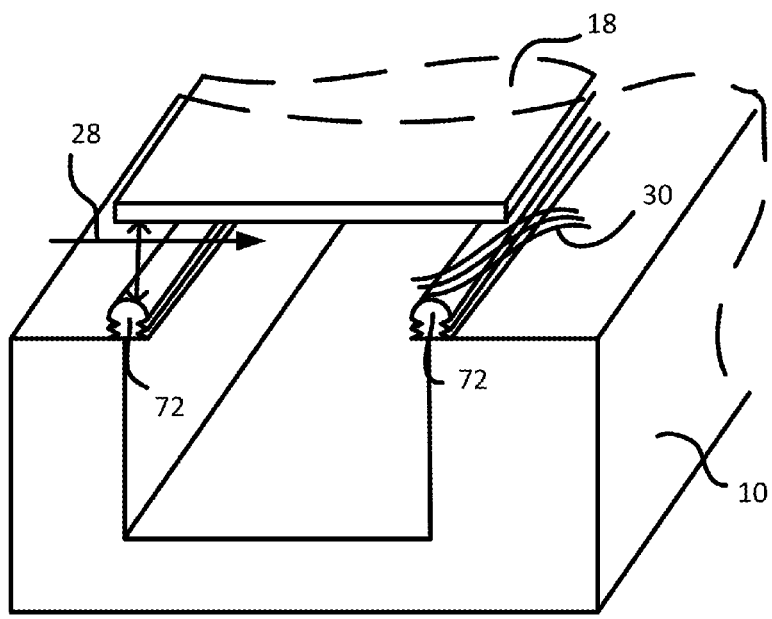

Referring to FIGS. 26 and 27, another embodiment is shown. Cover 18, in the closed position, contacts seal 72 sufficiently sealing the fluid container to restrict airflow into the interior of the fluid container. Seals 72 can be resilient materials and compressible to assist in restricting airflow. When cover 18 is open, space 64 is created and airflow 28 allows fragrance 30 to exit the fluid container and leave the room.

Referring to FIGS. 28 and 30, one embodiment is shown, Fragrance cartridge 74 is a container housing a fragrance medium impregnated with a fragrance. A sealing member 76 keeps the fragrance cartridge sealed until ready for use. The sealing member is removed and the fragrance cartridge is receiving by the housing and provide a fragrance container. There can be a plurality of receiving areas for multiple fragrance containers shown as 78a through 78d.

In one embodiment, a heating unit 80 is carried by the housing and, upon activation by the actuator, heats the fluid container to release a fragrance. Contacts can be in contact with the fragrance container and allow for the transfer of heat form the heating units to the medium when the cartridge is inserted into the housing. By using a heat activated fragrance medium, the fragrance life can be extended since the fragrance will only be released when the fragrance medium is heated rather than when exposed to the air. That actuator can turn on and off the heating unit based upon the user's selection of fragrance so that the fragrance medium is preserved.

While the invention has been described with reference to certain exemplary embodiments, obvious modifications and alternations are possible by those skilled in the related art. Therefore, it is intended that the invention include all such modifications and alterations to the full extent that they come within the scope of the following claims or the equivalents thereof.

What is claimed is:

1. A fragrance dispenser attachably connected to a fan comprising:
   a housing having openings defined in said housing;
   a fragrance reservoir included in said housing for receiving a fragrance medium containing a fragrance;
   a cover operably associated with said opening for restricting airflow into said fragrance reservoir;
   a cover actuator operably connected to said cover having an open position allowing airflow into and out of said fragrance reservoir for dispensing a fragrance and a closed position for restricting airflow into and out of said fragrance reservoir; and,
   a receiver in electronic communication with said cover actuator;
   a transmitter in communication with said receiver so that when said transmitter is actuated, an open signal is transmitted to said receiver and said cover actuator moves said cover to an open position.

2. The apparatus of claim 1 wherein:
   said fan is a ceiling fan having a standard; and,
   a standard opening defined in said housing for receiving said standard and securing said housing to said ceiling fan.

3. The apparatus of claim 1 including:
   a heating element carried by said housing for heating said fragrance media to release fragrance from said fragrance media.

4. The apparatus of claim 3 wherein said heating element is in electronic communication with said cover actuator so that said heating element is actuated when said cover is in said open position.

5. The apparatus of claim 2 wherein:
   said housing includes a first half and a second half;
   a magnet attached to said first half operably associated with a metal plate attached to said second half for securing said housing to said standard.

6. The apparatus of claim 1 including:
   an opening rod included in said cover actuator; and,
   a spring carried by said opening rod operably biasing said cover closed.

7. The apparatus of claim 6 including an electromagnet carried by said housing so that when electromagnet is energized, said opening rod opens said cover.

8. A fragrance dispenser attachably connected to a fan comprising;
   a housing having an opening and a fragrance container compartment defined in said housing;
   a cover operably connected to said opening for restricting airflow into said fragrance container;
   a cover actuator operably associated with said cover having an open position allowing airflow into and out of said fragrance container for dispensing fragrance and a closed position for restricting air flow into and out of said fragrance container; and,
   an opening rod included in said cover actuator;
   a spring carried by said opening rod operably biasing said cover closed.

9. The apparatus of claim 8 including a seal attached to said housing and operably associated with said cover for reducing airflow into and out of said fragrance container when said cover is in said closed position.

10. The apparatus of claim 9 wherein said seal is selected from the group comprising an o-ring, skirt, and resilient seal.

11. A fragrance dispenser attachably connected to a fan comprising:
    a housing having a plurality of openings defined in said housing;
    a plurality of fragrance reservoirs included in said housing, each associated with one of said openings;
    a plurality of covers, each operably associated with each one of said openings; and,
    a plurality of cover actuators operably connected to each one of said covers.

12. The apparatus of claim 11 including a plurality of seals carried by each one of said fragrance reservoirs taken from the group comprising an o-ring, skirt, and resilient seal.

13. The apparatus of claim 11 wherein said plurality of cover actuators cause said respective covers to move to an open position in series.

14. The apparatus of claim 11 including:
    a receiver carried by said housing and operably associated with said cover actuators; and,
    a transmitter in electronic communication with said receiver whereas said receiver will actuate at least one cover actuator when receiving an open command from said transmitter.

15. The apparatus of claim 14 wherein said receiver will actuate a second cover actuator when receiving a second open command from said transmitter.

16. The apparatus of claim 11 including a fragrance container removably received in said fragrance reservoir so that multiple fragrances can be placed in said fragrance reservoir.

17. The apparatus of claim 11 wherein said fan is selected from the group consisting of a box fan, desk fan, floor fan, wall fan, and ceiling fan.

18. The apparatus of claim 11 including a standard opening in said housing for receiving a standard of a ceiling fan for securing said housing to said ceiling fan.

19. The apparatus of claim 11 including a plurality of heating elements operatively associated with each of said fragrance reservoirs.

* * * * *